United States Patent [19]

Lebeau et al.

[11] Patent Number: 5,201,841
[45] Date of Patent: Apr. 13, 1993

[54] THERMAL DELAY NON-DESTRUCTIVE BOND INTEGRITY INSPECTION

[75] Inventors: Christopher J. Lebeau; Shay-Ping T. Wang, both of Tempe, Ariz.

[73] Assignee: Motorola, Inc., Schaumberg, Ill.

[21] Appl. No.: 838,643

[22] Filed: Feb. 20, 1992

[51] Int. Cl.[5] .................. G01N 25/00; G01N 25/20; G01N 29/00
[52] U.S. Cl. ........................ 374/5; 73/588; 374/4
[58] Field of Search ............. 374/4, 5, 6, 7; 73/588, 73/582, 598

[56] References Cited

U.S. PATENT DOCUMENTS

| | | | |
|---|---|---|---|
| 3,592,050 | 7/1971 | Nutt et al. | 73/582 |
| 4,007,631 | 2/1977 | Saifi et al. | 73/588 |
| 4,287,766 | 9/1981 | Ensminger | 73/582 |
| 4,289,030 | 9/1981 | Alers et al. | 73/588 |
| 4,513,384 | 4/1985 | Rosencwaig | 374/7 |
| 4,521,118 | 6/1985 | Rosencwaig | 374/5 |
| 4,522,510 | 6/1985 | Rosencwaig et al. | 374/7 |
| 4,641,527 | 2/1987 | Hiroi et al. | 73/582 |
| 4,710,030 | 12/1987 | Tauc et al. | 73/643 |
| 4,750,368 | 6/1988 | Shearer et al. | 73/588 |
| 4,972,720 | 11/1990 | Wu | 73/801 |

FOREIGN PATENT DOCUMENTS

| | | | |
|---|---|---|---|
| 0091554 | 4/1988 | Japan | 73/598 |
| 0304159 | 12/1988 | Japan | 73/598 |
| 2013344 | 8/1979 | United Kingdom | 73/598 |

OTHER PUBLICATIONS

Gilmore, et al., "High-Frequency Ultrasonic Testing of Bonds: Application to Silicon Power Devices," Materials Evaluation, pp. 65-72 (Jan. 1979).

Primary Examiner—William A. Cuchlinski, Jr.
Assistant Examiner—Diego F. F. Gutierrez
Attorney, Agent, or Firm—Joe E. Barbee

[57] ABSTRACT

A non-destructive method for testing quality of at least one bond which physically and electrically couples a package lead to an integrated circuit. A thermal gradient is created across the at least one bond which causes heat transfer thru the at least one bond. Heat transfer is measured which is proportional to area at a bond interface. The measured heat transfer thru the at least one bond is compared with heat transfer data taken under substantially equal conditions of known good bonds thereby determining quality of the at least one bond. The heat transfer is indirectly measured by creating a mechanical vibration at an input area and by measuring the time it takes the mechanical vibration to reach an output area after the mechanical vibration has traveled through the at least one bond.

8 Claims, 1 Drawing Sheet

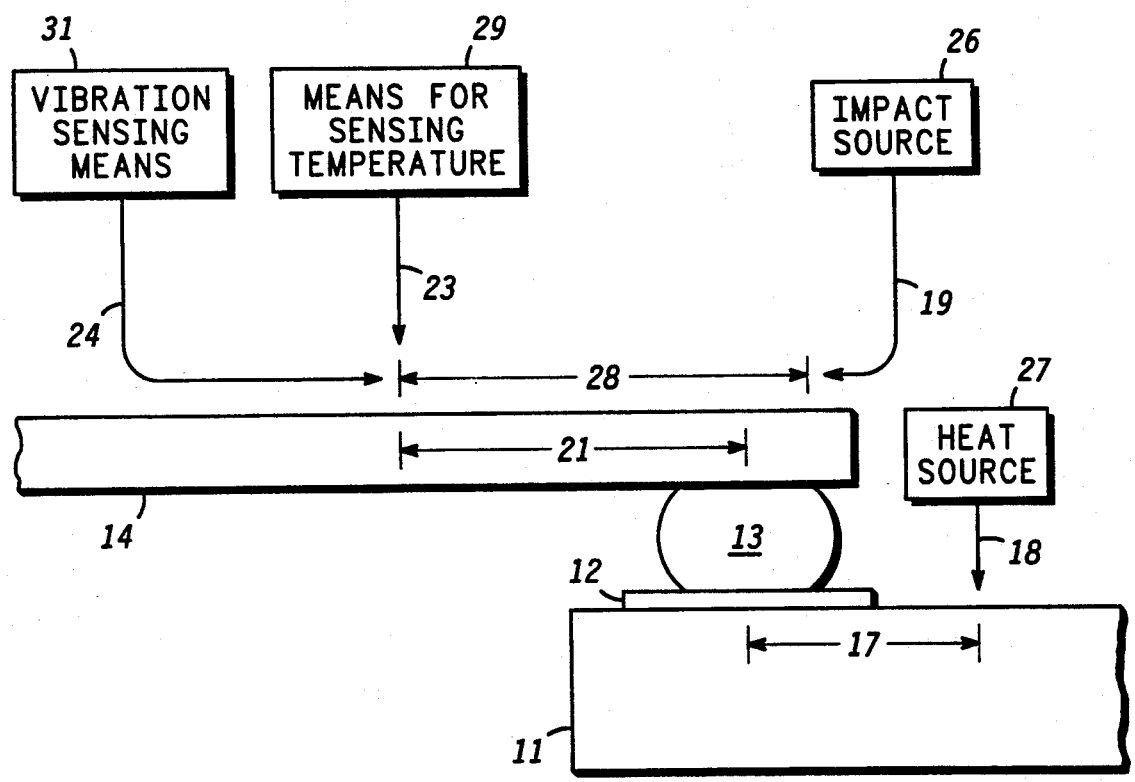

THERMAL DELAY NON-DESTRUCTIVE BOND INTEGRITY INSPECTION

BACKGROUND OF THE INVENTION

This invention relates, in general, to bond testing, and more particularly, to testing an electrical connection which is formed when a package lead is bonded to a pad area on a semiconductor device.

Increased functionality added to a semiconductor chip due to higher device densities will typically lead to an increased number of inputs and outputs. Packages are being developed to handle high numbers of inputs and outputs. Testing the integrity of bonds formed when package leads are bonded to the semiconductor chip will be critical to eliminating field failures due to defective bonds. Older methods for testing the integrity of the bonds may not work with new packages, be sufficient to insure long term reliability, or be fast enough for a production environment with high pin count packages.

For example, a high pin count package currently offered is known as a TAB package. The TAB package offers very tightly spaced leads which couple to a semiconductor device. Solder bumps are placed on pad areas of the semiconductor device. The TAB package leads align with the pad areas of the semiconductor device. The TAB leads are aligned to the pads such that a portion of the lead is placed above the solder bumps. The TAB package is lowered until the leads make contact to the solder bumps. A thermal cycle melts the solder bumps, coupling the leads to the semiconductor pads. Two interfaces are created, a TAB lead to solder bump, and solder bump to pad area, either of which could compromise quality of the device. An electrical test only confirms that a connection exists. Other methods must be used to determine the bond quality. The current test most widely used to measure a TAB bond is a destructive test. A package lead is physically separated from the solder and pad. The force needed to separate the bond is used to measure the bond integrity. By inference, the destructive test determines the quality of the remaining bonds.

It would be of some importance to provide a non-destructive method for determining the integrity of a bond. The method should be non-destructive, allow for individual bond testing, and be fast enough for use in a production environment.

SUMMARY OF THE INVENTION

Briefly stated, this invention provides a non-destructive test for evaluating the quality of a bond. A thermal gradient is created across a bond area to be evaluated. Temperature changes are recorded as heat is transferred through the bond area. The bond under evaluation can be characterized good or bad depending on the measured results correlation to known data of good and bad bonds.

An indirect method is used to determine temperature changes as heat is transferred through the bond area. The temperature changes can be calculated by utilizing an impact source which creates a mechanical wave through the package lead. The speed at which the wave travels can be related to temperature.

BRIEF DESCRIPTION OF THE DRAWINGS

The single figure is an illustration of a bond being tested in accordance with the present invention.

DETAILED DESCRIPTION OF THE DRAWINGS

The single figure illustrates the preferred embodiment of the method for sensing the quality of at least one bond. A semiconductor die 11 has a pad area 12, which is bonded to a package lead 14 by a solder bump 13. The single figure illustrates two bond interfaces. A first bond interface is formed where pad area 12 contacts solder bump 13. A second bond interface is formed where solder bump 13 contacts package lead 14. These two bond interfaces are in series between die 11 and package lead 14.

A heat source 27 heats a first input area indicated by an arrow 18. Heat source 27 serves as a means for imparting heat. The first input area is located a predetermined distance from the bond interfaces to be evaluated as indicated by a double headed arrow 17. The predetermined distance indicated by double headed arrow 17 is critical to insure measurements can be repeated under similar conditions. A transient or periodic heating of the first input area can be used in the method. Heat source 27 can be a laser, infra-red beam, or an electron beam. It is possible to eliminate heat source 27 by using heat at the bond create during the bonding process, if the bond test is performed immediately following the bonding process.

A thermal gradient is formed by heat source 27 across the bond interfaces. Heat transfer is monitored by a means for sensing temperature 29 at an output area indicated by an arrow 23. The output area is a predetermined distance from the bond interfaces as indicated by a double headed arrow 21. The predetermined distance indicated by double headed arrow 21 is critical to insure measurements can be repeated under similar conditions. It is critical to note that heat is transferred through the bond interfaces before reaching the output area where temperature changes are sensed. Also, heat is transferred serially through the first and second bond interfaces. Alternate paths which can circumvent the bond interfaces and increase thermal transfer to the output area should not be allowed. Means for sensing temperature 29 can be a laser or an infra-red beam.

A key factor in bond integrity is contact area at the bond interface. Ideally, both surfaces forming the bond will completely contact one another. A poor bond occurs when voids which reduce contact area at the bond interface occur. Heat transfer can be used as the method for sensing the quality of a bond because there is a direct correlation between heat transfer through the bond interface and the contact area at the bond interface. Larger contact area at the bond interface allows heat to be transferred faster. A comparison must be made between measurements taken on the tested bonds and data of known good and bad bonds to determine the quality of the tested bonds. The data from known good and bad bonds should be derived from identical bond types and measurements taken under identical conditions to preserve direct correlation.

Although the thermal time delay non-destructive bond integrity inspection involves sensing temperature at the output area with respect to time, it is not necessary to sense temperature directly. Depending on the equipment available it may be more accurate to use a different means of measurement from which the temperature of package lead 14 can be calculated. One such indirect method uses a mechanical disturbance. A mechanical disturbance can be created easily and monitored over time. It is well known that the speed at which a mechanical wave travels through a known material is a function of the material temperature. Average temperature of package lead 14 and temperature changes over time can be calculated using this technique. Like the direct approach, the indirect approach compares the measured data with data from known good and bad bonds.

In the preferred embodiment, an indirect method for sensing temperature at the output area is used. An impact source 26 is used to create a mechanical disturbance (or vibration) at a second input area indicated by an arrow 19. The second input area is a predetermined distance from the output area as indicated by double headed arrow 28. A vibration sensing means 31 is used to monitor waves set up by impact source 26 at the output area as indicated by an arrow 24. Impact source 26 can be a laser, ultrasound source, or an e-beam.

In the preferred embodiment, vibration sensing means 31 is a reflective probing laser which detects the waves created by impact source 26 by monitoring a reflection of a laser beam focused at the output area. Two equations are used in the indirect temperature sensing method to calculate the temperature of package lead 14. The first equation calculates the wave speed of the vibration through package lead 14. The second equation allows us to calculate the temperature of package lead 14 since the material and wave speed is known.

The wave speed sensed by vibration sensing means 31 can be calculated using a first equation $s = L/t$, where s is the speed of the wave, $L =$ the travel distance of the wave, and $t =$ the time duration of the wave. Distance L is indicated by double headed arrow 28.

Average temperature of package lead 14 is related to the wave to reach sensing means 31 after the wave is created by impact source 26, i.e., a certain time delay thereafter, as is well known, is indicated by the foregoing equation speed by a second equation $s = s' - (K)(T - T')$, where $s =$ speed of the wave, $T =$ Average temperature of package lead 14, $T' =$ a reference calibration temperature, $s' =$ a reference calibration speed of wave at $T'$, and $K =$ a coefficient which is material specific. The reference calibration temperature $T'$ is an ambient temperature. The reference calibration speed of wave at $T'$ is the speed of a wave measured at the ambient temperature.

Changes in package lead 14 temperature can be calculated from the two equations as heat is transferred through the bond region to package lead 14. Measured data is compared against data from known good and bad bonds (measured under identical conditions). How the measured time delay data compares with the known good and bad bond data determines the quality of the bond. Measuring temperature directly at the output area can lead to error due to thermal noise. Using the mechanical vibration technique to calculate temperature eliminates the thermal noise problem and provides a measurement of increased accuracy.

By now it should be appreciated that there has been provided a non-destructive method for testing a bond. The thermal technique is non-destructive, provides fast bond testing which can be used in a production environment, it can be completely automated, and is applicable to most bonds (TAB, wire, die, SMD, etc.) used in semiconductor packaging.

We claim:
1. A method for non-destructive bond integrity inspection for a semiconductor chip comprising:
    defining a bond evaluation path, wherein the bond evaluation path has a first input area located a predetermined distance from at least one bond, has a second input area located a predetermined distance from an output area, has a thermal path which passes serially through the at least one bond to be evaluated, and said output area being located a predetermined distance from the at least one bond.
    heating said first input area of the bond evaluation path which creates a thermal gradient across said at least one bond and said thermal path from the first input area to the output area;
    disturbing the second input area thereby creating a mechanical vibration for determining heat transfer through said at least one bond;
    measuring a time delay for an arrival of said mechanical vibration at said output area, said time delay corresponding to heat transfer through said at least one bond; and
    comparing said time delay to a plurality of time delays of known good bonds characterized under substantially equal conditions thereby determining said at least one bond integrity.
2. The method of claim 1 further including:
    choosing said bond evaluation path to eliminate thermal conductive paths which can circumvent thermal flow through said at least one bond to said output area.
3. The method of claim 1 wherein said heating said first input area step includes:
    using a laser to heat said first input area.
4. The method of claim 1 wherein said heating a first input area step includes:
    using an infra-red beam to heat said first input area.
5. The method of claim 1 wherein said heating a first input area step includes:
    using an electron beam to heat said first input area.
6. The method of claim 1 wherein said disturbing a second input area step includes:
    using a laser to disturb said second input area.
7. The method of claim 1 wherein said disturbing a second input area step includes:
    using ultrasound to disturb said second input area.
8. The method of claim 1 wherein said disturbing a second input area step includes;
    using an electron beam to disturb said second input area.

* * * * *